United States Patent [19]
Orr

[11] Patent Number: 5,865,768
[45] Date of Patent: Feb. 2, 1999

[54] GUIDE WIRE

[75] Inventor: Gregory C. Orr, Oceanside, Calif.

[73] Assignee: Medtronic, Inc., Minneapolis, Minn.

[21] Appl. No.: 723,408

[22] Filed: Sep. 30, 1996

[51] Int. Cl.⁶ ...................................................... A61B 5/00
[52] U.S. Cl. ........................... 600/585; 600/433; 604/95; 604/280
[58] Field of Search .............................. 128/772; 600/433, 600/434; 604/95, 76, 280, 281, 282

[56] References Cited

U.S. PATENT DOCUMENTS

| | | | |
|---|---|---|---|
| Re. 34,695 | 8/1994 | Mar et al. ................................ | 128/772 |
| 3,789,841 | 2/1974 | Antoshkiw .......................... | 128/2.05 R |
| 4,538,622 | 9/1985 | Samson et al. ........................... | 128/772 |
| 4,554,929 | 11/1985 | Samson et al. ........................... | 128/772 |
| 4,757,827 | 7/1988 | Buchbinder et al. .................... | 128/772 |
| 4,763,647 | 8/1988 | Gambale .................................. | 128/772 |
| 4,867,173 | 9/1989 | Leoni ....................................... | 128/772 |
| 5,144,959 | 9/1992 | Gambale et al. ........................ | 128/772 |
| 5,234,003 | 8/1993 | Hall ......................................... | 128/772 |
| 5,253,653 | 10/1993 | Daigle et al. ............................ | 600/585 |
| 5,345,945 | 9/1994 | Hodgson et al. ........................ | 128/772 |
| 5,353,808 | 10/1994 | Viera ....................................... | 128/772 |
| 5,460,187 | 10/1995 | Daigle ..................................... | 128/772 |

*Primary Examiner*—Max Hindenburg
*Assistant Examiner*—Pamela L. Wingood
*Attorney, Agent, or Firm*—Michael R. Shevlin; Dianne Plunkett Latham; Harold R. Patton

[57] ABSTRACT

The present invention is for a guide wire comprising a core wire with a first diameter and the distal end having at least one section having a second, lesser diameter and a radiolucent coil surrounding the distal end at the second core wire diameter with a radiopaque wire located at the distal end within the radiolucent coil and a means for securing the radiopaque wire to the core wire.

Another embodiment of the present invention is a guide wire comprising a core wire having a radiolucent portion and a radiopaque portion, the radiopaque portion being distal of the radiolucent portion and contiguous with the radiolucent portion, the proximal end of the core wire having a first diameter and the distal end having at least one step down diameter section, a radiolucent coil surrounding the step down diameter section of the core wire, the proximal end of the radiolucent coil being fixedly mounted to the proximal end of the step down diameter section of the core wire, and a tip ball fixedly attached to the distal end of the core wire and to the distal end of the radiolucent coil.

8 Claims, 1 Drawing Sheet

GUIDE WIRE

FIELD OF THE INVENTION

This invention relates to guide wires and more particularly to a guide wire with a radiopaque portion and a flexible distal end.

BACKGROUND OF THE INVENTION

Percutaneous transluminal coronary angioplasty (PTCA) is used to reduce arterial build-up of cholesterol fats or atherosclerotic plaque. According to this procedure, a blockage in a coronary artery can be reduced by positioning a balloon dilatation catheter across the blockage and inflating the balloon, which causes stretching of the artery and pressing of the lesion into the artery wall to re-establish acceptable blood flow through the artery. A guide wire is first inserted into the body and advanced through the desired coronary artery to reach a stenosis. Once the guide wire is positioned beyond the stenosis, the catheter is then slid over the guide wire so that placement of the balloon spans the stenosis and the balloon is then inflated.

Generally, guide wires have a solid core wire surrounded by one or more coil springs. The tip of the guide wire is usually shapable to allow the physician to bend the guide wire tip before insertion into the artery. The ease or difficulty of using the guide wire through the artery depends on several characteristics, such as steerability and tracking. A guide wire with superior steerability and tracking is easier to direct through a tortuous path to the stenosis. During the procedure, the guide wire is tracked by using an x-ray machine. To view the guide wire using the x-ray machine, a portion of the guide wire must be formed from a radiopaque material.

There are various ways to construct a guide wire for radiopacity. The most common way is to use spring coils mounted on the distal end of the guide wire that are radiopaque. There have been a number of patents directed to different constructions of guide wires including U.S. Pat. No. 4,757,827 to Buchbinder et al, U.S. Pat. No. 5,345,945 to Hodgson et al, U.S. Pat. No. 4,538,622 to Samson et al, U.S. Pat. No. Re. 34,695 to Mar et al and U.S. Pat. No. 5,353,808 to Viera.

One of the problems often encountered is that the guide wire has too long of a radiopaque section, making it very bright and blood flow difficult to see under x-ray. Some guide wires use multiple spring coils of different radiopacity. The problem with current multiple spring coil designs is at the joint between the coils. This same joint between the coils is also where the coils are joined to the core wire. This creates a non-flexible section on the wire in an area where the wire should have a smooth transition (See U.S. Pat. No. 5,345,945 and U.S. Pat. No. 5,353,808). What is needed is a guide wire that provides improved flexibility and a desirable amount of radiopaqueness.

SUMMARY OF THE INVENTION

It is an object of the invention to provide a new and improved guide wire that is constructed from a core wire having a first diameter at the proximal end and at least one section having a second, lesser diameter at the distal end. A radiolucent coil surrounds the distal end at the second core wire diameter. A radiopaque wire is located at the distal end of the core wire within the radiolucent coil with a means for securing the radiopaque wire to the core wire.

Another embodiment of the present invention is a guide wire having a core wire with a radiolucent portion and a radiopaque portion, the radiopaque portion being distal of the radiolucent portion and contiguous with the radiolucent portion, the proximal end of the core wire having a first diameter and the distal end having at least one step down diameter section, a radiolucent coil surrounding the step down diameter section of the core wire, the proximal end of the radiolucent coil being fixedly mounted to the proximal end of the step down diameter section of the core wire, and a tip ball fixedly attached to the distal end of the core wire and to the distal end of the radiolucent coil.

BRIEF DESCRIPTION OF THE DRAWINGS

The foregoing and other features of the present invention will be best appreciated with reference to the following detailed description of a specific embodiment of the invention, when read in conjunction with the accompanying drawings.

DETAILED DESCRIPTION OF THE PREFERRED EMBODIMENTS

The present invention is directed to a guide wire with improved distal flexibility with a radiopaque segment under the radiolucent coils. This is accomplished by using a radiopaque segment that is either part of the core wire or a separate radiopaque wire attached to the core wire along with a radiolucent coil covering the radiopaque segment. The advantage of having the radiopaque section under the radiolucent coil section it eliminates the difficulties associated with bonding multiple coils together and attaching the radiopaque segment before attaching the radiolucent coils will provide a more cost effective manufacturing method. Also disclosed is the use of a nonmetallic safety member. The advantage of the safety member is to ensure that the radiopaque segment of the core wire will not release into the artery in case it is detached.

Figure 1:
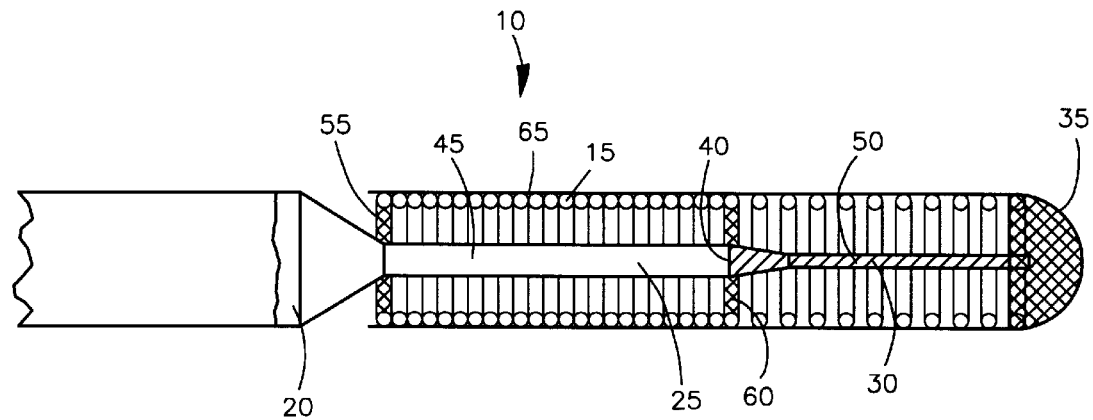
FIG. 1 is a view showing the present invention assembled.

FIG. 1 shows the distal end of the guide wire 10 consisting of a radiolucent coil 15, a core wire 20 with a radiolucent portion 25 and a radiopaque portion 30, and a tip ball 35. Along the length of the guide wire 10 is a torque-transmitting core wire 20 that is made of two materials. The radiolucent portion 25 is made from a 0.356 mm diameter (0.014") stainless steel wire, work hardened by drawing, or of shape memory wire such as nickel titanium. The radiopaque portion 30 is made from a 0.356 mm diameter (0.014") platinum, gold or other radiopaque wire. The radiolucent portion 25 and the radiopaque portion 30 are attached at joint 40. The joint 40 may use either adhesive, weld, braze, pin or screw. After joining the radiolucent portion 25 and the radiopaque portion 30, the diameter of the distal end of the core wire 20 is reduced with at least one step-down diameter to fit inside of the radiolucent coil 15. FIG. 1 shows a combination of multiple step-down diameters of 0.203 mm (0.008") 45 and 0.152 mm (0.006") 50. The distal end of the radiolucent coil 15, with an outer diameter of 0.356 mm (0.014") and an inner diameter of 0.254 mm (0.010") and an approximate length 30 cm, is welded to the distal end of the step down diameter 50 of the core wire 20 forming a tip ball 35. The tip ball 35 may also be a separate component that is fixedly attached to the distal end of the core wire 20 and radiolucent coil 15 using adhesive, weld or braze. The proximal end of the radiolucent coil 15 is then concentrically welded 55 to the proximal end of the step down diameter 45. Near the distal end of step down diameter 45 is an optional spring brace 60 that bonds the radiolucent coil 15 to the step down diameter 45 of the core wire 20. Locating the spring brace 60 at different locations along the step down diameter sections 45 and 50 will vary the flexibility of the distal end of the guide wire 10. The entire outside of guide wire 10 may be covered in a plastic, silicone or hydrophilic coating 65.

Figure 2:
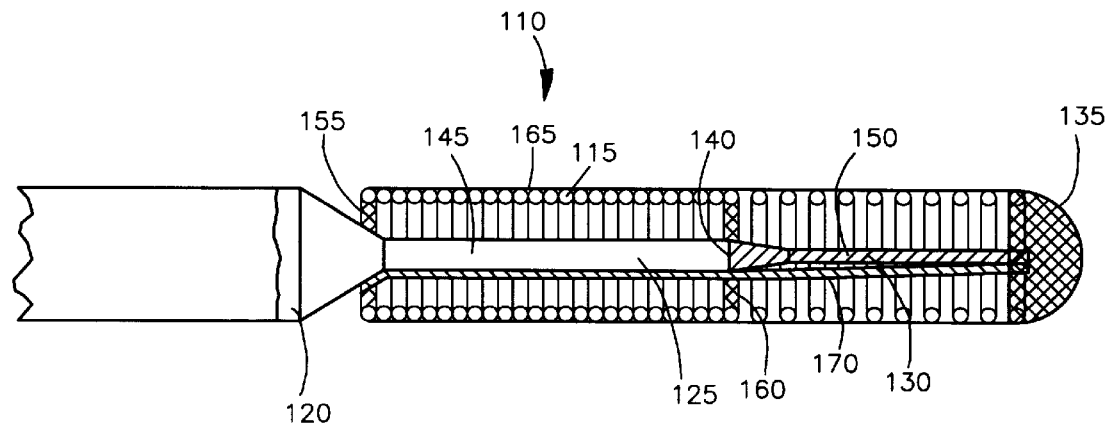
FIG. 2 is a view showing an alternate configuration present invention assembled.

FIG. 2 shows the distal end of the guide wire 110 consisting of a radiolucent coil 115, a core wire 120 with a radiolucent portion 125 and a radiopaque portion 130 and a tip ball 135. This is an alternate configuration to the invention shown in FIG. 1 with a safety member 170 being attached to the core wire 120. Along the length of the guide wire 110 is a torque-transmitting core wire 120 that is made of two materials. The radiolucent portion 125 is made from a 0.356 mm diameter (0.014") stainless steel wire, work hardened by drawing, or of shape memory wire such as nickel titanium. The radiopaque portion 130 is made from a 0.356 mm diameter (0.014") platinum, gold or other radiopaque wire. The radiolucent portion 125 and the radiopaque portion 130 are attached at joint 140. The joint 140 may use either adhesive, weld, braze, pin or screw. At the distal end of the core wire 120, the diameter is reduced with at least one step-down diameter to fit inside of the radiolucent coil 115. FIG. 2 shows a combination of multiple step-down diameters of 0.203 mm (0.008") 145 and 0.152 mm (0.006") 150. The distal end of the radiolucent coil 115, with an outer diameter of 0.356 mm (0.014") and an inner diameter of 0.254 mm (0.010") and an approximate length 30 cm, is welded to the distal end of the step down diameter 150 of the core wire 120 forming a tip ball 135. The tip ball 135 may also be a separate component that is fixedly attached to the distal end of the core wire 120 and radiolucent coil 115 using adhesive, weld or braze. The proximal end of the radiolucent coil 115 is then concentrically welded 155 to the proximal end of the step down diameter 145. Near the distal end of step down diameter 145 is a spring brace 160 that bonds the radiolucent coil 115 to the step down diameter 145 of the core wire 120. Locating the spring brace 160 at different locations along the step down diameter sections 145 and 150 will vary the flexibility of the distal end of the guide wire 110. The safety member 170 may be round, square or rectangular in shape and may be made of metallic or non metallic material such as kevlar or aramid fiber. The distal end of the safety member 170 is joined to the tip ball 135 and the proximal end of the safety member is joined to the spring brace 160. The proximal end of the safety member 170 may also extend and attached to the proximal end of the step down diameter 145 and the weld 155. The entire outside of guide wire 110 may be covered in a plastic, silicone or hydrophilic coating 165.

Figure 3:
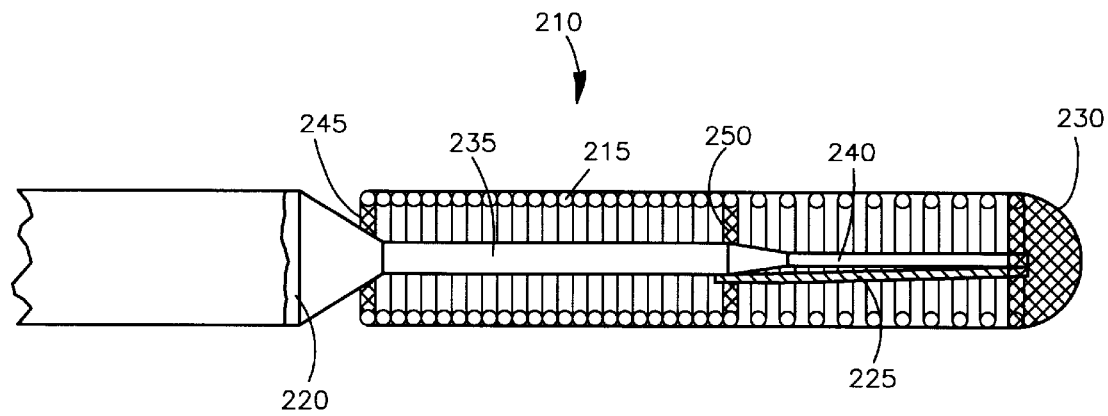
FIG. 3 is a view showing an alternate configuration present invention assembled.

FIG. 3 shows the distal end of the guide wire 210 consisting of a radiolucent coil 215, a core wire 220, a radiopaque wire 225 and a tip ball 230. This is an alternate configuration to the invention shown in FIG. 1 except that the core wire is one piece and a radiopaque wire 225 is added. Along the length of the guide wire 210 is a torque-transmitting core wire 220 that is made from a 0.356 mm diameter (0.014") stainless steel wire, work hardened by drawing, or of shape memory wire such as nickel titanium. The radiolucent wire may also be made of composite or polymer material. At the distal end of the core wire 220, the diameter is reduced with at least one step-down diameter to fit inside of the radiolucent coil 215. FIG. 3 shows a combination of multiple step-down diameters of 0.203 mm (0.008") 235 and 0.152 mm (.006") 240. The distal end of the radiolucent coil 215, with an outer diameter of 0.356 mm (0.014") and an inner diameter of 0.254 mm (0.010") and an approximate length of 30 cm, is welded to the step down diameter 240 at the distal end of the core wire 220, creating a tip ball 230. The tip ball 235 may also be a separate component that is fixedly attached to the distal end of the core wire 220 and radiolucent coil 215 using adhesive, weld or braze. The proximal end of the radiolucent coil 215 is then concentrically welded 245 to the proximal end of the step down diameter 235. Near the distal end of the step down diameter 235 is a spring brace 250 that bonds the radiolucent coil 215 to the step down diameter 235 of the core wire 220 and the radiopaque wire 225 such that the proximal end of the radiopaque wire 225 is joined to the spring brace 250 and the distal end of the radiopaque wire 225 is joined the to tip ball 230. The radiopaque wire 225 may be round, square or rectangular in shape and made of platinum, gold or other radiopaque material. The entire outside of the guide wire 210 may be covered with a plastic, silicone or hydrophilic coating 255.

The preceding specific embodiments are illustrative of the practice of the invention. It is to be understood, however, that other expedients known to those skilled in the art or disclosed herein, may be employed without departing from the scope of the appended claims.

No . Component
10 Guide Wire
15 Radiolucent coil
20 Core Wire
25 Radiolucent portion of Core Wire 20
30 Radiopaque portion of Core Wire 20
35 Tip Ball
40 Joint between 25 and 30
45 Step-down Diameter—Core Wire
50 Step-down Diameter—Core Wire
55 Weld—Radiolucent Coil to Step-down Diameter 45
60 Spring Brace
65 Plastic, Silicone or Hydrophilic Coating
110 Guide Wire
115 Radiolucent coil
120 Core Wire
125 Radiolucent portion of Core Wire 20
130 Radiopaque portion of Core Wire 20
135 Tip Ball
140 Joint between 25 and 30
145 Step-down Diameter—Core Wire
150 Step-down Diameter—Core Wire
155 Weld—Radiolucent Coil to Step-down Diameter 45
160 Spring Brace
165 Plastic, Silicone or Hydrophilic Coating
170 Safety Member
210 Guide Wire
215 Radiolucent coil
220 Core Wire
225 Radiopaque Wire
230 Tip Ball
235 Step-down Diameter—Core Wire
240 Step-down Diameter—Core Wire
245 Weld—Radiolucent Coil to Step down Diameter 235
250 Spring Brace

What is claimed is:
1. A guide wire comprising
(a) a core wire having a proximal end and a distal end, the proximal end of the core wire having a first diameter and the distal end of the core wire having at least one section having a second, lesser diameter than the first diameter;

(b) a radiolucent coil surrounding at least a portion of the core wire and including the section of second core wire diameter, the radiolucent coil extending to the distal end of the corewire;

(c) a radiopaque wire extending to a distal end of the guide wire, the radiopaque wire having a proximal end and a distal end, the proximal end of the radiopaque wire being affixed to a distal end of the core wire the radiolucent coil further extending to the distal end of the radiopaque wire; and (d) a means for securing the proximal end of the radiopaque wire to the distal end of the core wire and to the radiolucent coil at the same location.

2. A guide wire according to claim 1 further comprising:

(a) a core wire wherein the core wire proximal end has a radiolucent portion and a radiopaque portion, the radiopaque portion being distal of the radiolucent portion and contiguous with the radiolucent portion, the proximal end of the core wire having at least one step down diameter section, the radiopaque portion of the core wire having a length less than the length of the step down diameter section; and (b) the radiolucent coil surrounding the step down diameter section of the core wire, the radiolucent coil having a proximal end and a distal end, the proximal end of the radiolucent coil being fixedly mounted to the proximal end of the step down diameter section of the core wire.

3. A guide wire according to claim 2 further comprising: a spring brace attaching the radiolucent coil to the step down diameter of the core wire.

4. A guide wire according to claim 1 further comprising: a restraining means affixed to the core wire for preventing loss of the radiopaque wire.

5. The guide wire of claim 4 wherein the restraining means is a safety member having a proximal end and a distal end, the proximal end of the safety member being attached to the proximal end of the step down diameter section of the core wire and the distal end of the safety member being attached to the tip ball.

6. The guide wire of claim 5 wherein the safety member is made of kevlar.

7. The guide wire according to claim 1 wherein the distal end of the radiolucent coil is affixed to the distal end of the solid radiopaque wire by a welded attachment forming a tip ball.

8. The guide wire according to claim 1 wherein the radiopaque wire is a solid wire.

* * * * *

UNITED STATES PATENT AND TRADEMARK OFFICE
CERTIFICATE OF CORRECTION

PATENT NO. : 5,865,768
DATED : February 2, 1999
INVENTOR(S) : Gregory C. Orr

It is certified that error appears in the above-identified patent and that said Letters Patent is hereby corrected as shown below:

Column 4, Line 62, pg. 2, line 1 (Amendment): "comprising" should be "comprising:"

Signed and Sealed this

Twenty-eighth Day of December, 1999

Attest:

Q. TODD DICKINSON

Attesting Officer     Acting Commissioner of Patents and Trademarks